United States Patent [19]
Green et al.

[11] Patent Number: 5,197,970
[45] Date of Patent: * Mar. 30, 1993

[54] SURGICAL CLIP APPLICATOR

[75] Inventors: David T. Green; Richard A. McGarry, both of Norwalk, Conn.

[73] Assignee: United States Surgical Corporation, Norwalk, Conn.

[*] Notice: The portion of the term of this patent subsequent to Jul. 9, 2008 has been disclaimed.

[21] Appl. No.: 723,067

[22] Filed: Jun. 28, 1991

Related U.S. Application Data

[63] Continuation of Ser. No. 635,219, Dec. 27, 1990, Pat. No. 5,030,226, which is a continuation of Ser. No. 144,486, Jan. 15, 1988, abandoned.

[51] Int. Cl.$^5$ ............................................. A61M 17/08
[52] U.S. Cl. ..................................... 606/158; 606/139
[58] Field of Search ............... 606/120, 142, 143, 139, 606/151, 157, 158, 205, 206; 227/175, 176, 901, 902, 19

[56] References Cited

U.S. PATENT DOCUMENTS

| | | |
|---|---|---|
| 3,777,538 | 12/1973 | Weatherly ........................... 128/325 |
| 4,086,926 | 4/1978 | Green ............................... 128/334 R |
| 4,152,920 | 5/1979 | Green . |
| 4,166,466 | 9/1979 | Jarvik . |
| 4,242,902 | 1/1981 | Green . |
| 4,256,251 | 3/1981 | Moshofsky . |
| 4,296,751 | 10/1981 | Blake, III et al. . |
| 4,299,224 | 11/1981 | Noiles . |
| 4,316,468 | 2/1986 | Klieman et al. . |
| 4,325,376 | 4/1982 | Klieman et al. . |
| 4,430,997 | 2/1984 | DiGiovanni et al. . |
| 4,452,357 | 6/1984 | Klieman et al. . |
| 4,471,780 | 9/1984 | Menges et al. . |
| 4,478,220 | 10/1984 | DiGiovanni et al. . |
| 4,480,640 | 11/1984 | Becht . |
| 4,480,641 | 11/1984 | Failla et al. . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfus . |
| 4,549,544 | 10/1985 | Favaron . |
| 4,565,199 | 1/1986 | Becht . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,674,504 | 6/1987 | Klieman et al. . |
| 4,712,549 | 12/1987 | Peters et al. . |
| 4,850,355 | 7/1989 | Brooks et al. . |
| 5,030,226 | 7/1991 | Green et al. ..................... 606/158 |
| 5,049,152 | 9/1991 | Simon et al. ..................... 606/139 |

Primary Examiner—John D. Yasko
Assistant Examiner—William Lewis
Attorney, Agent, or Firm—Thomas R. Bremer

[57] ABSTRACT

The surgical clip applicator has a pusher bar which positions the foremost clip from a clip carrier into a ready-to-fire position between the jaws prior to squeezing of the handles together. When the applicator is fired, the previously positioned surgical clip can be crimped about a vessel and when the jaws are released, a new clip is placed between the jaws for the next firing. A channel assembly moves over the jaws to close the jaw while the pusher bar is retracted into the clip carrier for delivering the foremost clip from the carrier upon release of the handles. A latch arrangement is provided for locking the channel assembly in place and the handles against movement should the clip carrier be empty.

13 Claims, 8 Drawing Sheets

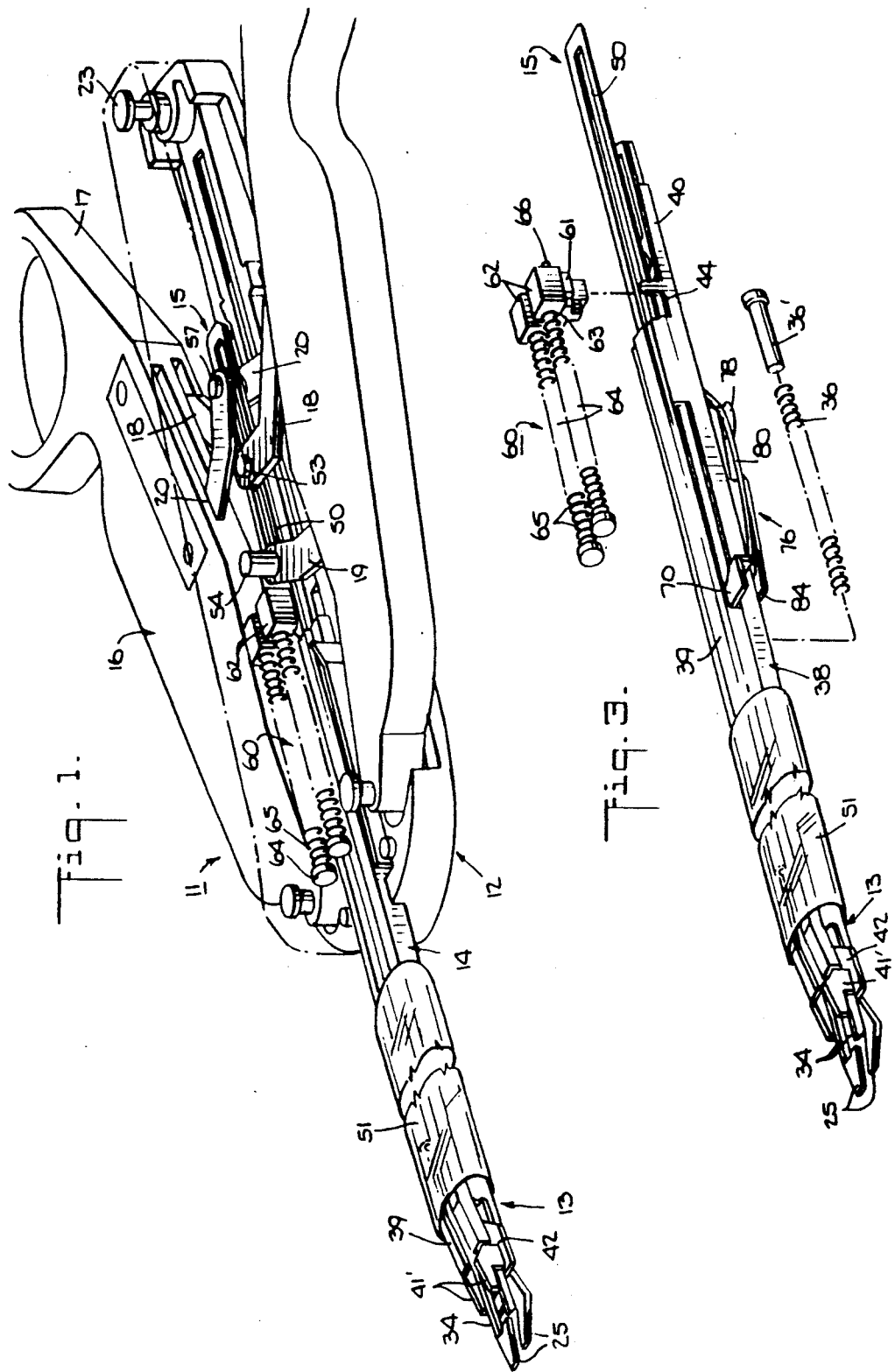

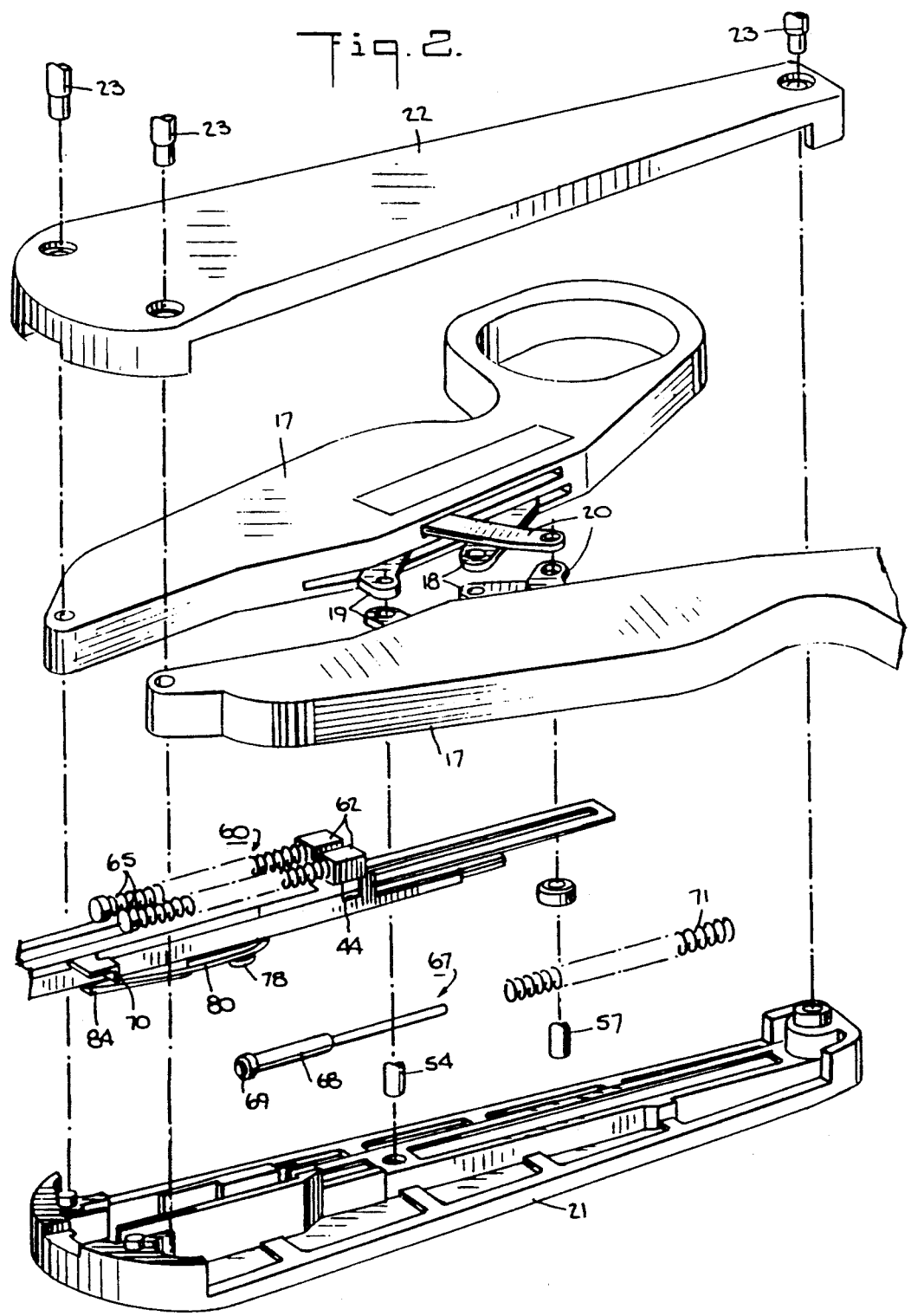

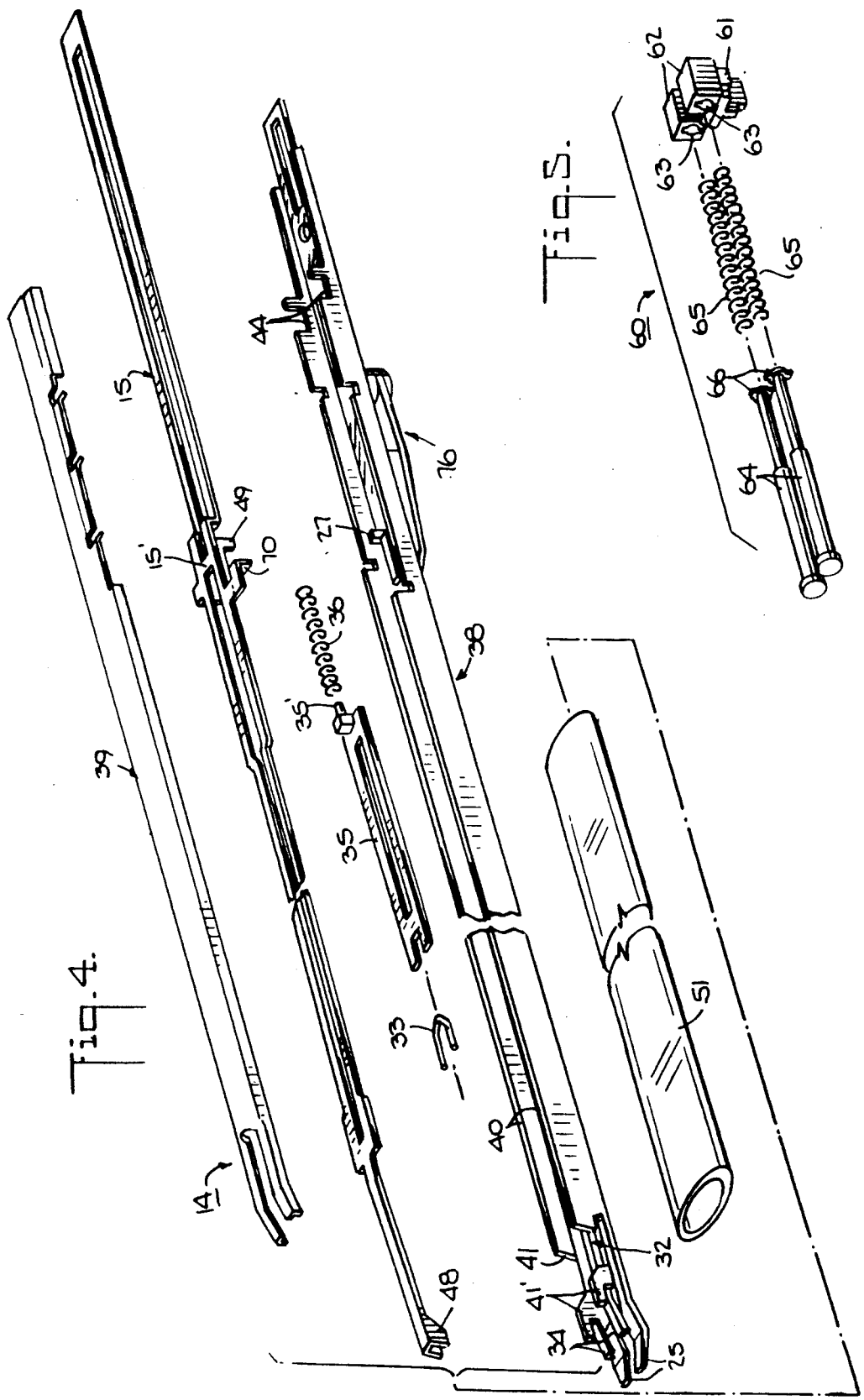

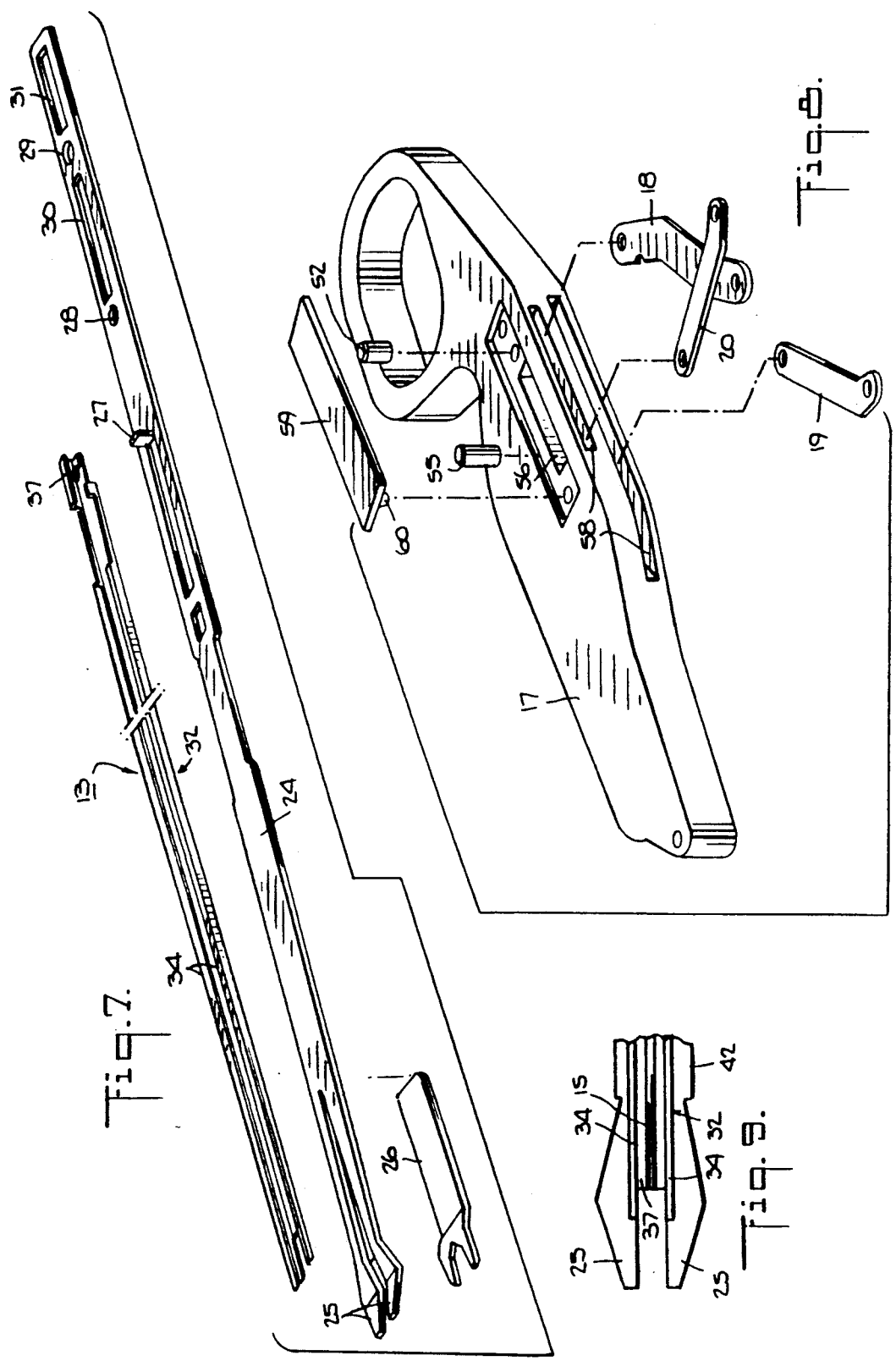

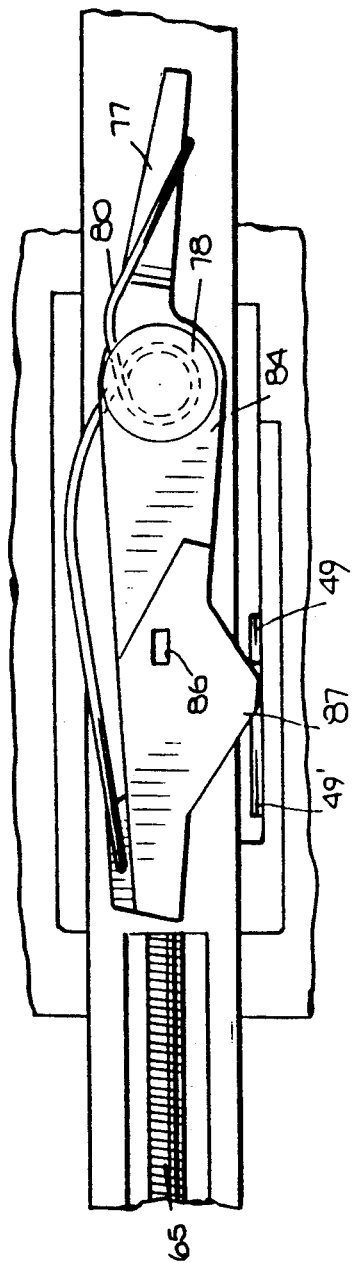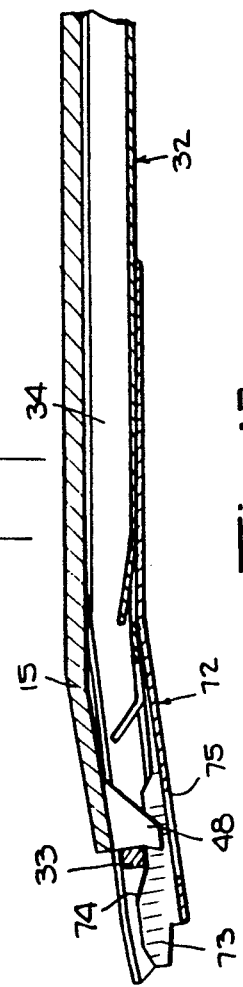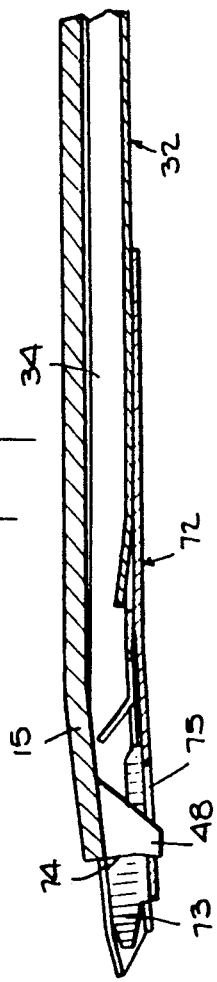

SURGICAL CLIP APPLICATOR

This is a continuation of U.S. application Ser. No. 07/635,219 filed Dec. 27, 1990, now U.S. Pat. No. 5,030,226, which is a continuation of 07/144,486 filed Jan. 15, 1988, abandoned.

This invention relates to a surgical clip applicator.

Heretofore, it has been known to use surgical clips, for example of metal, to provide hemostasis and occlude tissue structures in a wide variety of surgical procedures. To this end, use has been made of various applicators, for example.

To deliver a clip from a clip magazine to between a pair of jaws in response to the closing of a pair of handles by a surgeon with a subsequent crimping of the clip by the jaws via a continued closing of the handles together. However, such a pre-firing arrangement of a clip may pose problems to a surgeon. First, if the applicator has been completely discharged of clips, the surgeon may not be able to readily determine that the applicator is empty. Second, should an applicator be fired while about a vessel without a clip being discharged, the vessel may become damaged to such an extent that a clip cannot be subsequently applied at that location of the vessel. Third, the surgeon may not be able to see a clip being positioned between the jaws during closing of the handles to ensure proper position on a vessel.

Accordingly, it is an object of the invention to provide a surgical clip applicator in which a clip is positioned between a pair of jaws during a return stroke of the applicator and prior to the next firing sequence of operation.

It is another object of the invention to prevent the closing of the jaws of a clip applicator in the absence of a clip.

It is another object of the invention to position a clip between a pair of jaws of a clip applicator prior to positioning about a vessel or the like.

It is another object of the invention to facilitate the application of surgical clips during a surgical procedure.

It is another object of the invention to provide a smooth operating surgical clip applicator.

Briefly, the invention provides a surgical clip applicator which is constructed with a pair of jaws for receiving and deforming a clip therebetween, a clip carrier having a series of clips for delivery to the jaws, a pusher bar having a nose at a distal end and means for sequentially moving the pusher bar from an initial distal-most position with the nose behind a delivered clip between the jaws to a proximal-most position behind a foremost clip of the series and to the distal-most position to deliver the foremost clip between the jaws.

The means for sequentially moving the pusher bar may be in the form of a pair of handles which are articulated to the pusher bars and which are movable between an open position corresponding to the distal-most position of the nose and a closed position corresponding to the proximal-most position of the nose. In operation, the applicator would initially have a clip positioned between the jaws in a state ready for firing of the applicator. Thus, a surgeon could place the jaws of the applicator about a vessel and then squeeze the handles together in order to close the jaws on the clip. At the same time, the pusher bar would be moved in a proximal direction in order to engage behind the foremost clip in the carrier. Once the handles are released, the pusher bar would move in the distal direction to push the foremost clip in the carrier to a position between the jaws. The applicator would then be ready for a second firing.

The applicator can be constructed with a housing to which the handles are pivotally connected on opposite sides. In addition, the jaws may be part of a jaw blade assembly which is fixedly connected to the housing while a channel assembly is slidably mounted in the housing to envelope the jaw blade assembly with the pusher bar slidably mounted in the channel assembly in overlying relation to the clip carrier. In this embodiment, means are provided for moving the pusher bar and channel assembly relative to each other and to the jaws. This means includes not only the handles but also link means connected to and between the handles and the channel assembly for moving the channel assembly in a distal direction in response to closing of the handles together in order to move the jaws toward each other. In addition, a second link means is connected to and between the handles and the pusher bar for moving the pusher bar to a proximal-most position in response to closing of the handles together for positioning behind a foremost clip in the carrier and to a distal-most position in response to opening of the handles to position the foremost clip between the jaws. Further, the two link means may be articulated so as to move the channel assembly in the distal direction in advance of the proximal movement of the pusher bar.

Suitable springs may be provided in the housing for biasing the pusher bar in a distal direction and for biasing the channel assembly in a proximal direction such that the handles are also biased into an opened position.

In order to provide for locking of the jaws against movement towards each other in the absence of a clip in the clip carrier, the clip carrier is provided with a retaining means for receiving and retaining the nose of the pusher bar in a locked position while locking means are provided for blocking the jaws against movement towards each other in response to the pusher bar being retained in the locked position.

The retaining means for the nose of the pusher bar may be in the form of a channel shaped member with a pair of upstanding parallel walls shaped to form a cam surface for the clip to ride on with an opening in the floor fastened to the underside of the carrier near the distal-most position of the nose and into which the nose is biased in the absence of clips in the carrier.

The locking means includes a detent on the channel assembly and a pivotally mounted latch in the housing for engaging the detent with the pusher bar located in the locked position in order to prevent distal movement of the channel assembly. Once the locking means has been activated, the channel assembly is prevented from moving in the distal direction so that the jaws cannot be closed. At the same time, the handles are prevented from being moved towards each other. This provides a positive indication to a surgeon that the applicator is empty of surgical clips.

The locking means may also include means to block actuation of the locking means during normal use of the applicator. In this regard, the blocking means includes a detent on the pusher bar for blocking the latch from engaging with the channel assembly detent when the pusher bar is in the distalmost position and for permitting engagement of the latch when the pusher bar nose is in the locked position. During an operation, so long as there are surgical clips in the carrier, the pusher bar will move the foremost clip forwardly, i.e. distally into a position between the jaws as the handles of the applicator are opened. After the last clip has been delivered into a position between the jaws, the next firing of the applicator will result in the pusher bar being retracted, i.e. moved proximally, into the empty clip carrier. As the handles are subsequently opened, the nose of the pusher bar will slide along the floor of the clip carrier and drop into the opening near the end of the carrier and thus be prevented from moving to the distal-most position. Thus, the detent on the pusher bar will not move into a blocking position relative to the latch for engaging the channel assembly. This latch will then drop into position under the bias of a spring so as to prevent distal, i.e. forward movement of the channel assembly and at the same time prevent the handles from being moved together. This will signal to the surgeon that the applicator is empty and can be discarded.

These and other objects and advantages of the invention will become more apparent from the following detailed description taken in conjunction with the accompanying drawings wherein:

FIG. 1 illustrates a part perspective view of an applicator constructed in accordance with the invention;

FIG. 2 illustrates a partial exploded view of the applicator of FIG. 1;

FIG. 3 illustrates a perspective view of a jaw blade assembly and channel assembly of the applicator constructed in accordance with the invention;

FIG. 4 illustrates an exploded view of the jaw blade assembly and channel assembly;

FIG. 5 illustrates a spring assembly for biasing the channel assembly in a proximal direction;

FIG. 7 illustrates an exploded view of the clip carrier and jaw blade;

FIG. 8 illustrates a part perspective view of one handle and articulated linkage therefore; and FIG. 9 illustrates a partial plan view of the distal end of the applicator of FIG. 1;

FIG. 10 illustrates a bottom view of the locking means in accordance with the invention:

FIG. 11 illustrates a cross sectional view of a retaining means in accordance with the invention with a clip being discharged from a clip carrier;

FIG. 12 illustrates a view similar to FIG. 11 in the absence of a clip;

Figure 6:
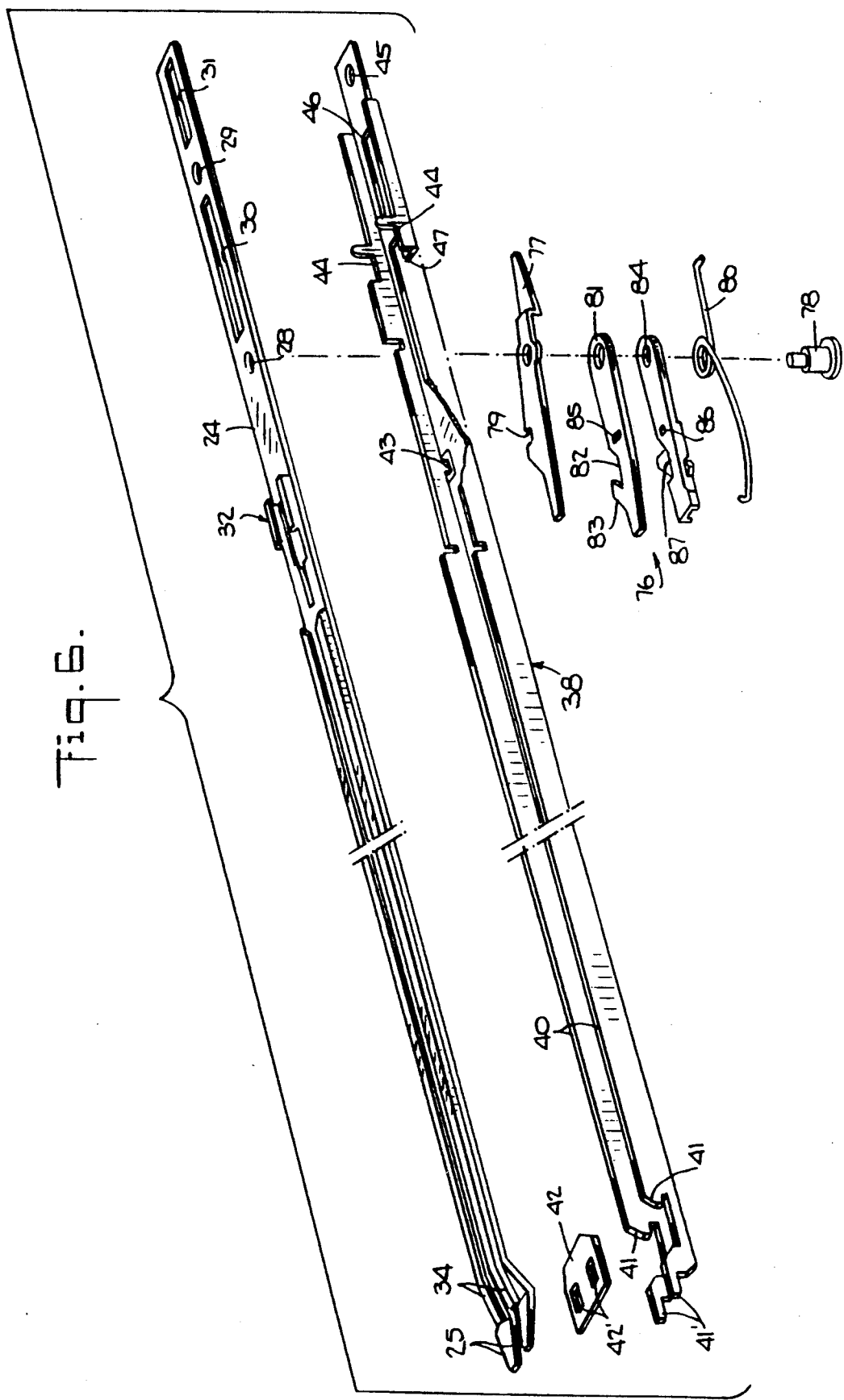
FIG. 6 illustrates an exploded view of the jaw blade assembly, clip carrier, channel assembly and latches for the pusher bar and channel assembly.

Referring to FIG. 1, the surgical clip applicator 11 includes a housing 12, a jaw blade assembly 13 fixedly connected to the housing 12, a channel assembly 14 slidably mounted in the housing 12 and enveloping the jaw blade assembly 13, a pusher bar 15 slidably mounted in the channel assembly 14 and means 16 for moving the pusher bar 15 and the channel assembly 14 relative to each other. The means 16 for moving the channel assembly 14 and pusher bar 15 includes a pair of handles 17 pivotally connected to opposite sides of the housing 11 by link means in the form of a pair of links 18 connected to and between the handles 17 and the channel assembly 14 for moving the channel assembly in a distal, i.e. forward, direction in response to closing of the handles 17 together and a second link means in the form of two pairs of links 19, 20 connected to and between the handles 17 and the pusher bar 15 for moving the pusher bar 15 to a proximal-most position in response to closing of the handles 17 together.

Referring to FIGS. 1 and 2, the housing 12 is formed of a bottom 21 and a top 22 which are secured together as by three rivets 23. This housing 12 is of slender construction and is made of any suitable material, for example, a plastic material. As indicated, the housing bottom 21 is contoured and recessed so as to receive various components of the applicator as further explained below. The housing top 22 is contoured for similar purposes.

The handles 17 are pivotally connected at the distal ends to opposite sides of the housing 11 by means of the pair of rivets 23 at the forward end of the housing.

Referring to FIG. 7, the jaw blade assembly 13 includes an elongated jaw blade 24 which has a pair of upwardly angled jaws 25 formed at a bifurcated distal end for receiving a surgical clip therein. As is conventional, each jaw 25 is provided with a small slot or groove in a side wall so as to receive a leg of a substantially U-shaped surgical clip therein. In addition, a tissue stop 26 is disposed below the jaws 25 and extends proximally under the jaw blade 24. This tissue stop 26 has a bifurcated distal end which underlies and serves as a guide to prevent tissue from impeding movement of the clip 33 (FIG. 4) into jaws 25. The jaw blade 24 is shaped so that the jaws 25 can be cammed towards each other and spring-biased apart.

The jaw blade 24 is also provided with an upstanding abutment 27 at an intermediate point to act as a distal stop for the pusher bar 15. In addition, the rear end of the jaw blade 24 is provided with an alternating sequence of circular openings 28, 29 and elongated slots 30, 31 for purposes as explained below.

The jaw blade assembly 13 also includes a clip carrier 32 for supplying a series of clips 33 to the jaws 25. This clip carrier 32 is formed as an elongated channel having a pair of side walls or rails 34 between which the clips 33 are slidably guided, a pusher 35 (see FIG. 4) which slides between the rails 34 and a spring 36 for biasing the pusher 35 in a distal direction. As indicated in FIGS. 3 and 4, the spring 36 is mounted about a shaft 36' has a head to abut at the proximal end against an abutment 37 of the clip carrier 32 (FIG. 7) and fits over a stem 35, on the pusher 35 in order to bias the pusher 35 in the forward direction.

Referring to FIG. 9, the rails 34 are aligned with the jaws 25 and are angled downwardly so as to deliver a clip directly from between the rails 34 to directly between the jaws 25 and are spaced apart a distance equal to the spacing between the jaws 25.

Referring to FIG. 4, the channel assembly 14 includes an elongated channel shaped member 38 and a cover 39 which is fixed secured to the channel shaped member 38 in order to envelope the jaw blade assembly 13 of FIG. 7.

As indicated in FIG. 6, the channel 38 has a pair of upstanding parallel walls 40 which extend to a distal end. Each wall 40 is shaped at the distal end to form a recess 41 and an axially extending projection 41'. A capture plate 42 is fitted into and across the recesses 41 of the walls 40 while having a pair of apertures 42' to fit over the projections 41'. As indicated in FIGS. 1 and 9, the capture plate 42 serves to hold down the jaw blade 24 and is disposed between the jaw blade 24 and the clip carrier 32. Also, as indicated in FIG. 1, the channel cover 39 is inclined downwardly at the distal end in alignment with the distal ends of the walls 40.

In addition, the channel 38 has a depending detent 43 (see FIG. 6) at an intermediate point of the bottom of the channel 38 as well as a pair of recesses 44 formed in the walls 40 towards the proximal end. In addition, the proximal end of the channel 38 is formed with a circular opening 45 and two elongated slots 46, 47.

Referring to FIG. 4, the pusher bar 15 is of elongated shape and has a depending nose 48 at the distal end. As indicated, the forward end of the pusher bar 15 is angled slightly downwardly from the remainder of the bar 15 and is located above the clip carrier 32 so as to slide on the bottom of the carrier 32. In addition, the pusher bar 15 has a depending detent 49 which is secured thereto in any suitable fashion. This detent 49 is shaped as indicated in FIG. 10 to extend rearwardly, i.e. in the proximal direction for purposes as explained below and has a secondary detent 49' at the distal end. As illustrated, the proximal end of the pusher bar 15 is provided with an elongated slot 50.

Referring to FIGS. 1 and 4, a sleeve 51 in the form of a shrink-fitted plastic tube is disposed about the channel assembly 14 for conventional purposes.

Referring to FIG. 1, each handle 17 is articulated to the housing 12, the channel assembly 14 and the pusher bar 15 in similar relation. Hence, only one articulation will be discussed. As indicated in FIG. 8, each channel link 18 is pivotally mounted at the proximal end about a pivot pin 52 which is fixed within the handle 17 while being pivotal about a pivot pin 53 (see FIG. 1) at the distal end which is secured in the circular opening 45 of the channel 38 of the channel assembly 14 (see FIG. 6). Thus, when the handles 17 close together, the two channel links 18 push the channel assembly 14 (see FIG. 1) forwardly in the distal direction. At this time, the channel assembly 14 slides over the jaws 25 to close the jaws 25 together so as to crimp a clip 33 positioned therebetween.

Each pusher bar link 19 is pivotally mounted about a fixed pin 54 mounted in the housing 11 (see FIG. 2). In addition, the proximal end of each link 19 is pivotally mounted about a pivot pin 55 which is slidably mounted within an elongated groove or channel 56 in the handle 17. The pivot pin 55 also receives the distal end of the pusher bar link 20. The proximal end of this link 20 is mounted about a common pin 57 (see FIGS. 1 and 2) which, in turn, slides within the elongated slot 50 of the pusher bar 15.

As indicated in FIG. 8, each handle 17 is provided with two slots 58 to accommodate the links 18, 19, 20. In addition, a cover plate 59 is mounted over an opening in each handle via depending pins 60 to close off the groove 56 and cover over the assembly opening.

When the handles 17 are brought together, the links 18 slide the channel assembly 14 forward (distally) while the links 19, 20 initially expand apart so that the pin 57 of link 20 (see FIG. 1) slides within the slot 50 of the pusher bar 15 until abutting against the proximal end of the pusher bar 15. Thereafter, the pusher bar 15 is moved in the proximal, i.e. rearward direction relative to the housing 11. Thus, when the handles 17 are first brought together, the channel assembly 14 moves forwardly and after a slight delay, the pusher bar 15 begins to move proximally. For example, the channel assembly 14 moves approximately 0.060 inches before the pusher bar 15 begins to move.

Referring to FIGS. 1 and 5, a spring assembly 60 is provided in the housing 12 in order to bias the channel assembly 14 in a proximal direction against the force of the handles 17. As indicated in FIG. 5, the spring assembly 60 is formed of a backing block 61, for example of plastic which has a pair of upstanding ears 62 through each of which a bore 63 passes. In addition, a pair of shafts 64 extend through the bores 63 of the block 61 and receive compression springs 65 thereon. Each shaft 64 has an enlarged head at the distal end for abutting against a suitable abutment surface of the housing top 22 (not shown) as well as a flanged stop 66 at the proximal end for sub-assembly purposes. As indicated in FIG. 3, the backing block 61 is mounted in the channel assembly 14 and specifically within and across the recesses 44 formed in the walls 40 of the channel 38.

Referring to FIG. 2, a spring assembly 67 is also provided for biasing the pusher bar 15 in the distal direction. To this end, the spring assembly 67 has a shaft 68 which has an enlarged and shouldered head 69 at the distal end which fits into an opening of a depending lug 70 on the pusher bar 15 as well as a spring 71 which fits over a reduced postion of the shaft 68 and which abuts against a suitable abutment (not shown) in the housing bottom 21. As indicated in FIG. 3, the lug 70 projects through a slot in the channel assembly 38 formed by a reduced section of a wall 40 and the cover 39.

Referring to FIGS. 11 and 12, a retaining means 72 is provided on the carrier 32 in order to retain the nose 48 of the pusher bar 15 when the carrier 32 has been emptied. The retaining means 72 is in the form of a channel-shaped member which is secured to the underside of the carrier 32 and which has a pair of upstanding walls 73, each of which provides a cam surface 84 for sliding of a clip 33 thereon. The member also has an opening 75 formed in the floor which is sized to receive the nose 48 of the pusher bar 15 in the absence of a clip 33.

Referring to FIG. 4, a locking means 76 is provided for blocking the jaws 25 against movement towards each other in response to the nose 48 of the pusher bar 15 being retained in the locked position, i.e. in the opening 75 (see FIG. 12). This position is obtained when there are no longer any clips 33 in the clip carrier 32 In this respect the distal end of the pusher bar 15 is spring biased into the clip carrier 32 so that when clips 33 are present, the distal most clip 33 is pushed by the pusher bar nose 48 onto and across the cam surface 74 of the upstanding walls 73 of the retaining means 72 which cams the retaining means away from the distal end of the pusher bar 15 thus allowing the nose 48 to pass over the opening 75 when a clip is being pushed forwardly into and between the jaws 25. However, with no clips remaining, the retaining means 72 is not cammed away from the distal end of the pusher bar 15, thus not allowing the nose 48 to pass over the opening 75 but to drop into the opening 75 stopping the forward motion of the pusher bar 15.

As shown in FIG. 6, he locking means 76 includes a latch 77 which is pivotally mounted about a rivet 78 which is fixed to the circular opening 28 of the jaw blade 24. As indicated, the rivet 78 extends upwardly into the circular opening 28 of the jaw blade 24 as well as through the elongated slot 47 in the channel 38 of the channel assembly 14. The latch 77 is pivotally mounted below the channel 38 and has a recess 79 for selectively engaging with the depending detent 49 of the pusher bar 15 (see FIG. 10). In addition and shown in FIG. 13D, the latch 77 is spring biased by a spring 80 so as to pivot in a clockwise manner as viewed so as to engage with the detent 49' of the pusher bar 15 when the pusher bar 15 is in its proximal position preventing premature feeding of the distal most clip into the jaws 25.

The locking means 76 also includes a second latch 81, for example of sheet metal, which is pivotally mounted on the rivet 78 in parallel relation to the latch 77. This latch 81 has a recess 82 and a cam surface 83 forward of the recess 82 to cooperate with the depending detent 43 of the channel 38 of the channel assembly 14.

The locking means 76 also includes an elongated cam follower 84, for example of plastic which is also pivotally mounted above the rivet 78 in single-arm fashion. This cam follower 84 is fixed to the latch 81 via a detent 85 of the latch 81 fitting into a rectangular hole 86 in the follower 84 so as to pivot therewith and includes a cam surface 87 of triangular shape which faces toward the detent 49 of the pusher bar 15 when the applicator is in a normally opened position. In addition, the cam follower 84 is biased by one end of the spring 80 in a clockwise direction (as viewed) to bias the latch 81 towards engagement with the detent 43.

Figure 13A:
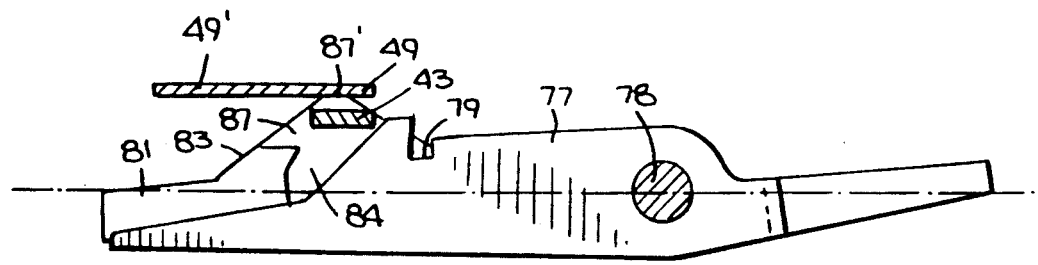
FIG. 13A illustrates a normal position of the locking means.
Figure 13B:
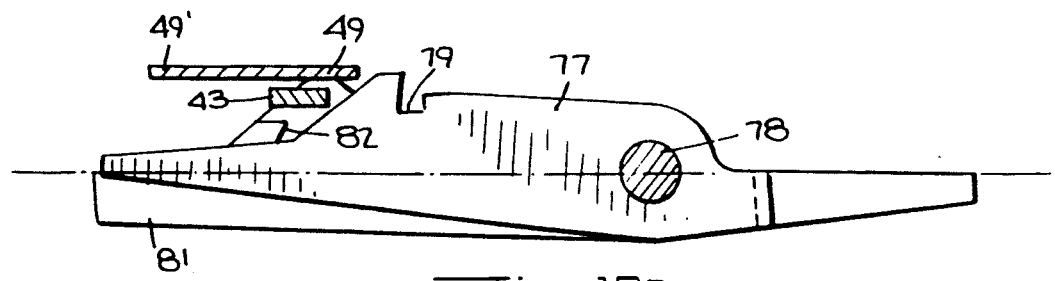
FIG. 13B illustrates a position of the locking means upon initial squeezing of the handles.
Figure 13C:
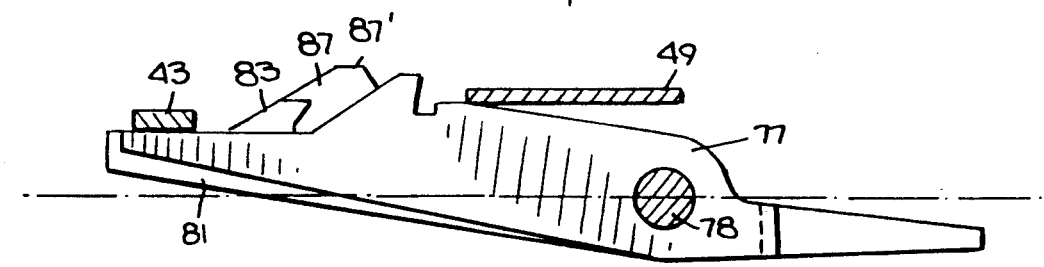
FIG. 13C illustrates a position of the locking means with the handles fully closed.
Figure 13D:
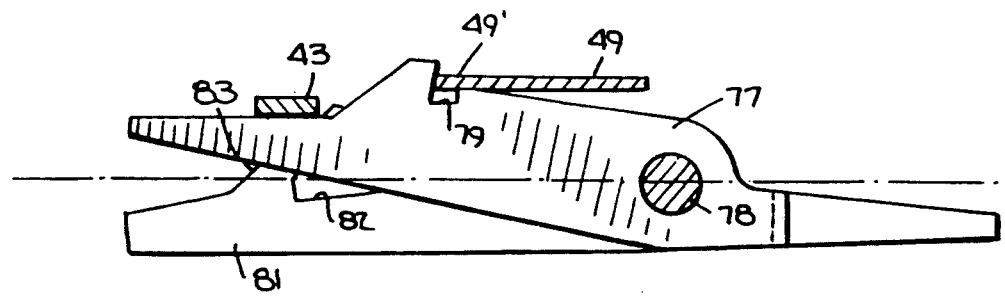
FIG. 13D illustrates a position of the locking means during a return stroke.
Figure 13E:
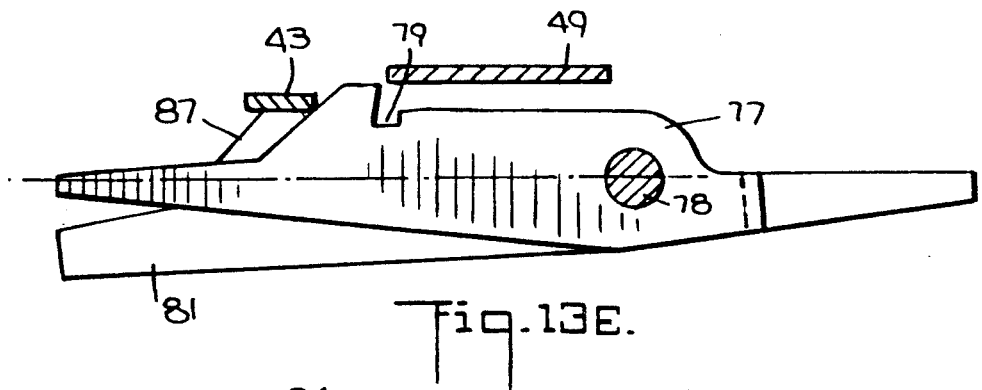
FIG. 13E illustrates a position of the locking means at the release point of the pusher bar.
Figure 13F:
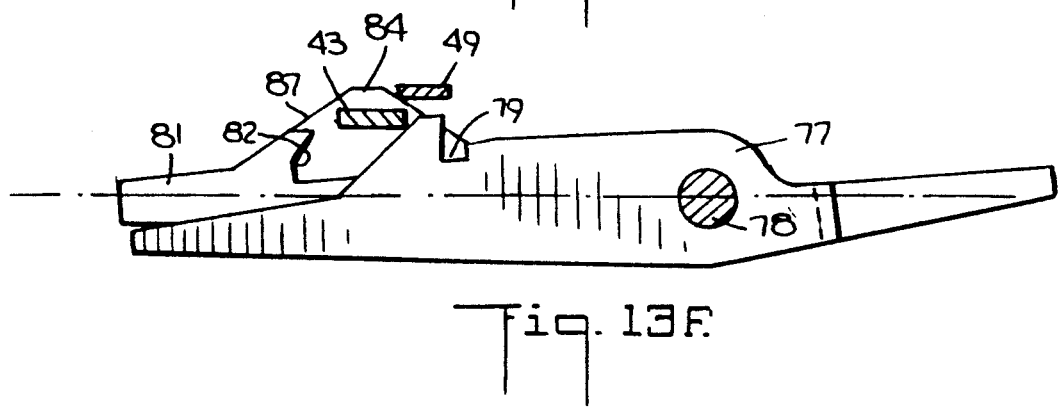
FIG. 13F illustrates a position of the locking means with a clip at a distalmost position in the clip carrier.

Should the clip carrier 32 contain clips 33, the nose 48 of the pusher bar 15 will normally be placed in a distal-most position immediately behind the jaws 25. At this time, the detent 49 on the pusher bar 15 will be located against the high point 87' of the cam surface 87 of the cam follower 84 (see FIG. 13A). Thus, the latch 81 for locking the channel assembly 14 in place will be out of line with the detent 43. As the handles 17 (see FIGS. 13B and 13C) are squeezed together, the pusher bar detent 49' will slide proximally past the recess 79 of the latch 77 while the detent 43 of the channel assembly 14 slides distally past the recess 82 of the latch 81. As the handles open with clips in the clip carrier 32, the detent 43 of the channel assembly 14 slides on the cam surface 83 into alignment with the recess 82 of the latch 81 (FIGS. 13D, E and F). At the same time, the detent 43 of the channel assembly 14 rotates the latch 77 counter clockwise releasing detent 49' distally. As the pusher bar 15 moves distally, the detent 49 comes in contact with the cam surface 87 of the cam follower 84 rotating the cam follower 84 counter clockwise as the pusher bar 15 moves distally moving surface 82' of recess 82 of the latch 81 out of line with detent 43 of the channel assembly 14. When the pusher bar is at its distal most position (FIG. 13F), the distal side of a cross bar 15' of the pusher bar 15 (see FIG. 4) abuts the proximal side of the jaw abutment 27.

Figure 14:
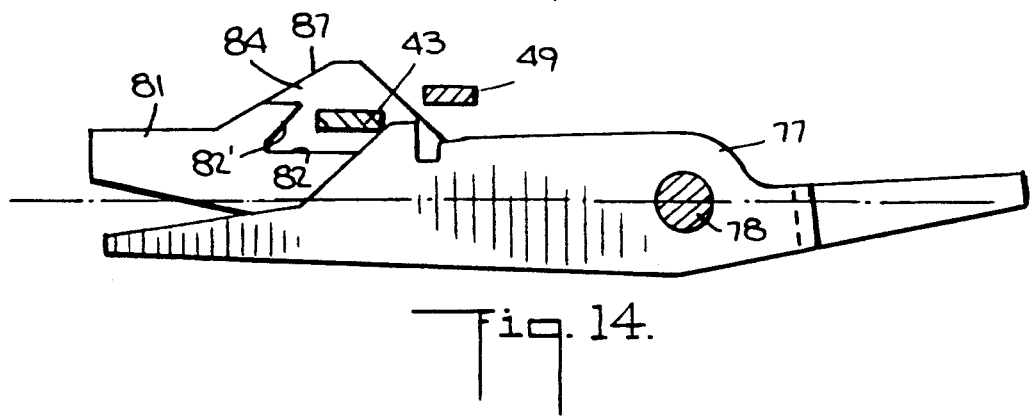
FIG. 14 illustrates a position of the locking means with no clip in the carrier.
Figure 15:
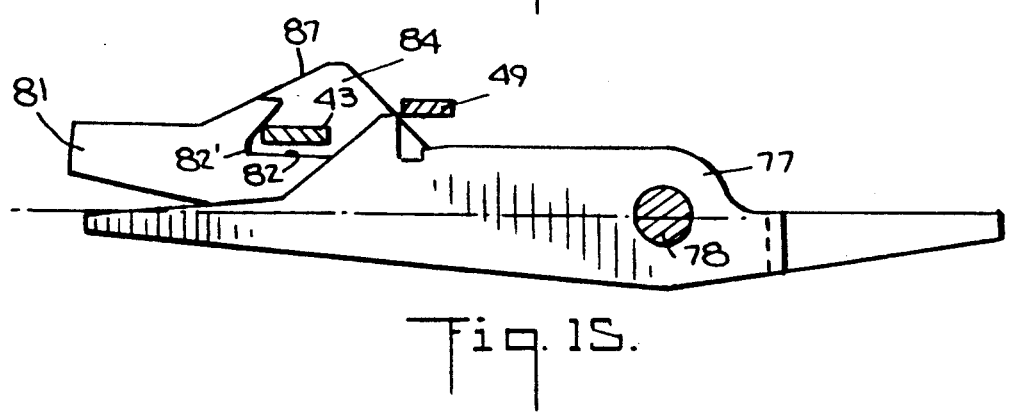
FIG. 15 illustrates a position of the locking means upon partial squeezing of the handles in the locked position.

However, should the clip carrier 32 be empty, the nose 48 of the pusher bar 15 will drop into the opening 75 causing the detent 49 to stop at a position away from cam surface 87 of the follower 84 leaving surface 82' of recess 82 of latch 81 in line with detent 43 of channel 38 (FIG. 14) upon a subsequent initial squeezing together of the handles of the applicator (FIG. 15), the spring biased latch 81 and associated cam follower 84 will be in a position such that surface 82, of recess 82 of the latch 81 will impede the movement of the detent 43 of the channel assembly 14. In this respect, the detent 49 of the pusher bar 15 is not in a position against the cam surface 87 so as to preclude a clockwise pivoting motion. Thus, as the handles are squeezed further, the detent 43 comes into contact with surface 82' of the recess 82 of the latch 81 causing latch 81 to rotate clockwise and is prevented from further distal motion. The jaws 25 can, thus, not be brought together and the handles are prevented from a further closing movement.

When the applicator 11 is to be used, the handles are first squeezed together causing the channel assembly 14 to move forwardly and the pusher bar 15 to move rearwardly into a position to feed the first clip 33 from the carrier 32. As the pusher bar 15 starts to move rearwardly, the pusher bar latch 77 is biased to rotate into the path of the detent 49 on the pusher bar 15 and after passage of the detent rearwardly thereby prevents the pusher bar 15 from moving forward prematurely. As the handles are released, the channel assembly 14 moves in the rearward direction on a return stroke while the pusher bar 15 remains stationary until the channel assembly 14 has moved close to its rearward position at which time the depending detent 43 of the channel 38 rotates the pusher bar latch 77 in an opposite direction, i.e. counter clockwise as viewed in FIG. 6, releasing the pusher bar 15 to feed the first clip 33 between the jaws 25. At this time, the pusher bar 15 springs forwardly under the bias of the spring assembly 67 (see FIG. 2) with the nose 48 passing over the opening 75 in the retaining means 72 since the clip 33 in the carrier 32 moves the retaining means 72 away from the bar 15 allowing the nose 48 to pass over the opening 75 of the retaining means. With the applicator 11 thus prepared, a surgeon will be able to see a clip in place and can then apply the clip where desired by squeezing the handles 17 together. At this time, when the handles are released, the next clip in the carrier is pushed into place between the jaws.

The invention thus provides a surgical clip applicator which is able to provide a clip between the jaws of the applicator in a ready position for firing upon squeezing of the handles together. This initial positioning of the clip in place permits a surgeon not only to visually check to see if a clip is present in the jaws but also permits the surgeon to position the clip about a vessel or other tissue which is to be clipped.

The invention further provides a surgical clip applicator which has a self-locking arrangement which prevents closing of the handles together when there are no clips remaining in the applicator.

Still further, the invention provides a surgical clip applicator which is of relatively simple compact and slender construction which can be readily manipulated by a surgeon during a surgical procedure.

What is claimed is:

1. A surgical clip applicator comprising:
   a housing;
   at least one handle pivotably mounted to said housing for movement between an open position and a closed position;
   a jaw blade assembly extending from said housing and including a pair of jaws for receiving and deforming a clip;

a channel assembly slidably mounted in at least a portion of said housing for movement between a proximal position and a distal position for enveloping said pair of jaws;

a pusher bar slidably mounted within at least a portion of said housing for feeding a clip to said jaws;

first means connected to said at least one handle for moving said pusher bar proximally in response to movement of said at least one handle towards said closed position; and second means connected to said at least one handle for moving said channel assembly distally upon movement of said at least one handle towards said closed position to thereby close said jaws;

wherein said pusher bar feeds a clip to said jaws upon movement of said at least one handle from said closed position to said open position.

2. A surgical clip applicator as recited in claim 1, wherein said channel assembly moving means comprises at least one link, said at least one link having an aperture to receive a mounting pin for mounting said link.

3. A surgical clip applicator as recited in claim 1, wherein said pusher bar has a forward end angled downwardly with respect to a rear end.

4. A surgical clip applicator as recited in claim 1, further comprising spring means for biasing said channel assembly in a proximal direction and spring means for biasing said pusher bar assembly in a distal direction.

5. A surgical clip applicator as recited in claim 1, further comprising means for blocking movement of said pusher bar when said clip carrier is emptied of clips.

6. A surgical clip applicator as recited in claim 5, wherein said blocking means comprises an opening formed in said clip carrier for receiving a distal end of said pusher bar.

7. A surgical clip applicator as recited in claim 1, wherein said channel assembly includes a channel having a pair of upstanding parallel walls.

8. A surgical clip applicator as recited in claim 1, further comprising a pair of handles, said handles being movable to a closed position by pivoting both said handles inwardly towards each other.

9. A surgical clip applicator as recited in claim 1, wherein said pusher bar has an elongated slot formed therein to receive said pusher bar moving means.

10. A surgical clip applicator as recited in claim 9, wherein initial movement of said channel assembly occurs in advance of initial movement of said pusher bar.

11. A surgical clip applicator as recited in claim 1, further comprising a clip carrier for holding a plurality of clips.

12. A surgical clip applicator as recited in claim 1, wherein said first moving means and said second moving means are pivotably connected to said at least one handle.

13. A surgical clip applicator as recited in claim 1, wherein said pusher bar and said channel assembly move substantially concurrently.

* * * * *